United States Patent [19]

Weiler

[11] 4,172,893
[45] Oct. 30, 1979

[54] RODENTICIDAL 3-PYRIDYLMETHYL PHENYL CARBAMATE METAL SALT COMPLEXES

[75] Inventor: Ernest D. Weiler, Ambler, Pa.

[73] Assignee: Rohm and Haas Company, Philadelphia, Pa.

[21] Appl. No.: 868,651

[22] Filed: Jan. 11, 1978

Related U.S. Application Data

[63] Continuation-in-part of Ser. No. 642,422, Dec. 19, 1975, abandoned.

[51] Int. Cl.$^2$ ............................................. A01N 9/22
[52] U.S. Cl. ...................................... 424/263; 424/84; 546/12; 546/329; 546/330; 546/334; 546/335
[58] Field of Search ......................... 424/263, 84, 266; 260/294.8 F, 295.5 C; 546/12, 329, 330, 334, 335

[56] References Cited

U.S. PATENT DOCUMENTS 3,865,931   2/1975   Ware et al. ............................ 424/263

3,966,947   6/1976   Kilbourn et al. ..................... 424/263

OTHER PUBLICATIONS

Kirk–Othmer Encyc. of Chem. Tech., vol. 16, (1968), pp. 786–787.

*Primary Examiner*—V. D. Turner
*Attorney, Agent, or Firm*—Susan Borden Evans

[57] ABSTRACT

Complexes of 3-pyridylmethyl 4-substituted-phenylcarbamates with salts of an alkaline earth or transition metal are useful as rodenticides. The carbamates from which the complexes are prepared have the formula

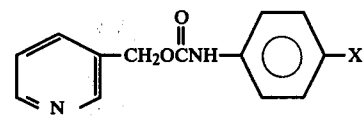

wherein X is a nitro, cyano, trifluoromethyl, alkylsulfinyl, alkylsulfonyl, or aminosulfonyl group.

9 Claims, No Drawings

RODENTICIDAL 3-PYRIDYLMETHYL PHENYL CARBAMATE METAL SALT COMPLEXES

CROSS REFERENCE TO RELATED APPLICATION

This application is a continuation-in-part of my copending application Ser. No. 642,422, filed Dec. 19, 1975, now abandoned.

This invention is concerned with novel metal salt complexes of 3-pyridylmethyl 4-substituted-phenylcarbamates which are biologically active, especially in controlling pest rodents.

The novel metal salt complexes of the invention are prepared from 3-pyridylmethyl 4-substituted-phenylcarbamates of the formula

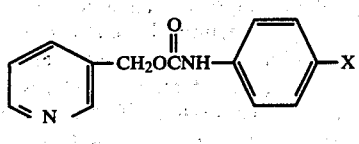

(I)

wherein
X is —NO$_2$, —CN, —CF$_3$, —SOR, —SO$_2$R, or —SO$_2$NH$_2$
wherein
R is a branched, or straight-chain alkyl group, preferably of up to 4 carbon atoms;
and metal salts of the formula $$MY_n \qquad (II)$$

wherein
M is a cation of an alkaline earth or transition metal, such as barium, cadmium, calcium, cobaltous, cupric, ferrous, ferric, magnesium, manganous, mercuric, nickel, stannous, stannic, zinc, or the like;
Y is an anion forming a salt with the cation M in which the salt has sufficient solubility to form a complex with the carbamate, such as bromide, chloride, iodide, perchlorate, carbonate, bicarbonate, nitrate, phosphate, sulfate, bisulfate, acetate, maleate, oxalate, p-toluenesulfonate, or the like; and
n is an integer which for the anion X satisfies the valence for the cation M.

These complexes may generally be represented by the formula (III)

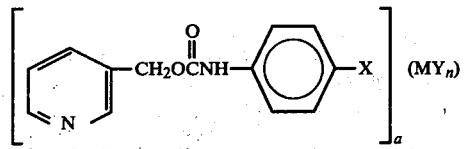

wherein X, M, Y, and n are as defined above, and a is 1 or 2.

The preferred complexes are the calcium, cupric, nickel, zinc, magnesium, and ferrous complexes, most preferably the calcium chloride, cupric chloride, nickel chloride, zinc chloride, magnesium bromide, and ferrous sulfate complexes.

The metal salt complexes of this invention are particularly useful as rodenticides. The 3-pyridylmethyl 4-substituted-phenylcarbamate precursors of these metal salt complexes have rodenticidal activity. The metal salt complex derivatives do, however, have advantages. They are distinct chemical compounds which possess increased stability over their carbamate precursors. As a rule the metal salt complex has a higher melting point than the corresponding carbamate and this is partly responsible for the increased stability of the metal salt complex. When the parent carbamate degrades for example, upon being subjected to heat, it at least in part may revert to its components 3-pyridylcarbinol and a 4-substituted aniline. The presence of impurities of this type have been known to render a rodenticidal bait less acceptable by the rodent.

The relatively high melting point of each metal salt complex of this invention also allows the technical product to be easily tabletized or formulated without danger of decomposition into its component parts. Accordingly any means of rendering an active rodenticide of this carbamate type more stable without seriously affecting its toxicity to the rodents is desirable, and the metal salt complexes of this invention accomplish this.

In addition, it appears that by means of the metal salt complexes of this invention, a slow release of the 3-pyridylmethyl 4-substituted-phenylcarbamate is achieved. This becomes advantageous when single-dose rodenticides which give a relatively rapid kill are involved. For example, after the rodent has eaten a lethal dose it is desirable that he has time to return to his home base before becoming too incapacitated to move. In this manner, bait shyness will be minimized since the rodent will die away from the bait surroundings, and the dead carcasses will not become an unsightly nuisance.

The 3-pyridylmethyl 4-substituted-phenylcarbamate metal salt complexes of this invention are readily made by allowing a solution of a 3-pyridylmethyl 4-substituted-phenylcarbamate to react with a solution or slurry of the appropriate metal salt. The preferred solvents are alcohols such as methanol, ethanol, isopropanol and 2-methoxyethanol. However, any solvent in which the reactants have sufficient solubility, preferably of at least 5% by weight, and which are inert can be used. Anhydrous conditions are preferred and the anhydrous grade of the metal salt is almost always used. It is often necessary to warm the metal salt or the 3-pyridylmethyl 4-substituted-phenylcarbamate and the solvent to achieve solution. Temperatures up to 100° C. are quite satisfactory and the reaction can be carried out without cooling if desired. The reaction can be run in the temperature range of about 0° to about 100° C., although ambient temperatures are usually preferred. The product often precipitates as the reaction proceeds or upon cooling and can be conveniently isolated by filtration. In cases where the reaction product is soluble in the reaction solvent, isolation is achieved by partial or complete evaporation of the solvent. The preparation of the 3-pyridylmethyl 4-substituted-phenylcarbamate precursors to the present complexes is described in U.S. Pat. No. 3,865,931, granted Feb. 11, 1975, to Ware et al., and in patent application Ser. No. 478,678, filed June 12, 1974, by Ware et al., which are incorporated herein by reference.

The following examples will further illustrate this invention, but are not intended to limit it in any way. All parts and percentages are by weight and all temperatures in degrees Centigrade unless otherwise indicated.

EXAMPLE 1

Preparation of Cupric Chloride Complex of 3-Pyridylmethyl N-(4-nitrophenyl)carbamate To a filtered, warm solution of 2.7 g. (0.01 mole) of 3-pyridylmethyl N-(4-nitrophenyl)carbamate in 400 ml. of the monomethyl ether of ethylene glycol (glyme) is added a solution of 1.3 g. (0.01 mole) of anhydrous CuCl$_2$ in 15 ml. of glyme. Cooling gives a precipitate which is isolated by filtration to give 2.9 g. of a blue solid melting at 270°–272° C. The product is an 85% yield of 3-pyridylmethyl N-(4-nitrophenyl)carbamate-cupric chloride complex.

EXAMPLE 2

Preparation of Cadmium Chloride Complex of 3-Pyridylmethyl N-(4-nitrophenyl)carbamate When cadmium chloride is substituted for cupric chloride in the procedure of Example 1, there is obtained 3.3 g. of white solid melting at 270° C. with decomposition. The product is considered to be a 73% weight yield of 3-pyridylmethyl N-(4-nitrophenyl)carbamate-cadmium chloride complex.

EXAMPLE 3

Preparation of Zinc Chloride Complex of 3-Pyridylmethyl N-(4-nitrophenyl)carbamate When zinc chloride is substituted for the cupric chloride in the procedure of Example 1, there is obtained 2.3 g. of a white solid melting at 185°–189° C. with decomposition.

EXAMPLES 4–9

Following the procedure of Example 1, the following metal salt complexes of 3-pyridylmethyl N-(4-cyanophenyl)-carbamate are prepared:
4. ZnCl$_2$
5. ZnBr$_2$
6. CuCl$_2$
7. MnCl$_2$
8. Cu(NO$_3$)$_2$
9. NiCl$_2$ Following the procedures of Examples 1 to 9 above, other metal salt complexes can be prepared from salts of the formula MY$_n$, where M, Y, and n are as defined above as reacted with
3-pyridylmethyl N-(4-nitrophenyl)carbamate
3-pyridylmethyl N-(4-trifluoromethylphenyl)carbamate
3-pyridylmethyl N-(4-methylsulfinylphenyl)carbamate
3-pyridylmethyl N-(4-ethylsulfinylphenyl)carbamate
3-pyridylmethyl N-(4-propylsulfinylphenyl)carbamate
3-pyridylmethyl N-(4-butylsulfinylphenyl)carbamate
3-pyridylmethyl N-(4-methylsulfonylphenyl)carbamate
3-pyridylmethyl N-(4-ethylsulfonylphenyl)carbamate
3-pyridylmethyl N-(4-propylsulfonylphenyl)carbamate
3-pyridylmethyl N-(4-butylsulfonylphenyl)carbamte and
3-pyridylmethyl N-(4-aminosulfonylphenyl)carbamate Typical metal salts used in these preparations are barium chloride, cadmium chloride, calcium bisulfate, calcium bicarbonate, calcium p-toluenesulfonate, calcium chloride, calcium maleate, cobaltous chloride, cobaltous bromide, cupric bromide, cupric chloride, cupric nitrate, ferrous oxalate, ferrous phosphate, ferrous sulfate, ferric sulfate, ferric nitrate, magnesium chloride, magnesium nitrate, magnesium iodide, magnesium perchlorate, maganese carbonate, mercuric chloride, nickel chloride, stannous bromide, stannous chloride, stannic chloride, zinc acetate, zinc chloride, zinc bromide, and the like.

Table I gives the structure and melting or decomposition points of typical examples of this invention and Table II give the analytical data calculated and found for these examples.

TABLE I

Metal salt Complexes of 3-Pyridylmethyl 4-Substituted-Phenyl Carbamates

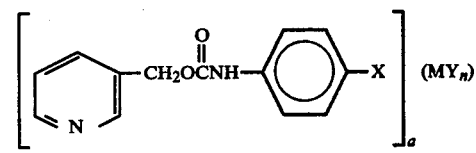

| Example | X | a | M | Y | n | Melting Point (°C.) |
|---|---|---|---|---|---|---|
| 1 | —NO$_2$ | 2 | Cu | Cl | 2 | 270–272 |
| 2 | —NO$_2$ | 1 | Cd | Cl | 2 | >260 |
| 3 | —NO$_2$ | 2 | Zn | Cl | 2 | 185–189 |
| 4 | —CN | 2 | Zn | Cl | 2 | 218–220 |
| 5 | —CN | 2 | Zn | Br | 2 | 240–242 |
| 6 | —CN | 2 | Cu | Cl | 2 | 250–252 |
| 7 | —CN | 2 | Mn | Cl | 2 | 200–205 |
| 8 | —CN | 2 | Cu | NO$_3$ | 2 | 240–242 (dec.) |
| 9 | —CN | 2 | Ni | Cl | 2 | 220–222 (dec.) |

TABLE II

Analytical Data on Examples

| Example | Empirical Formula | % C | % H | % N | % Metal | % Cl |
|---|---|---|---|---|---|---|
| 1 | C$_{13}$H$_{11}$N$_3$O$_4$ · ½CuCl$_2$ | 45.69(45.82) | 3.53(3.25) | 12.24(12.34) | Cu 9.28(9.33) | 10.54(10.41) |
| 2 | C$_{13}$H$_{11}$N$_3$O$_4$ · CdCl$_2$ | 37.36(34.27) | 2.70(2.43) | 10.22(9.22) | Cd 19.23(24.67) | 12.02(15.56) |
| 3 | C$_{13}$H$_{11}$N$_3$O$_4$ · ½ZnCl$_2$ | 45.88(45.87) | 3.66(3.25) | 11.63(12.35) | | 10.39(10.41) |
| 4 | C$_{14}$H$_{11}$N$_3$O$_2$ · ½ZnCl$_2$ | 52.63(52.32) | 3.40(3.45) | 13.06(13.07) | Zn 8.17(10.17) | 10.07(11.03) |
| 5 | C$_{14}$H$_{11}$N$_3$O$_2$ · ½ZnBr$_2$ · ½H$_2$O | 44.91(44.86) | 3.37(3.20) | 11.05(11.21) | | |
| 6 | C$_{14}$H$_{11}$N$_3$O$_2$ · ½CuCl$_2$ | 52.22(52.47) | 3.46(3.46) | 12.98(13.10) | Cu 9.21(9.91) | 10.05(11.06) |
| 7 | C$_{14}$H$_{11}$N$_3$O$_2$ · ½MnCl$_2$ | 53.23(53.19) | 3.76(3.50) | 13.30(13.28) | Mn 6.24(8.69) | 9.34(11.21) |

TABLE II-continued

| | | Analytical Data on Examples | | | | |
| | Empirical | | | Analysis* | | |
| Example | Formula | % C | % H | % N | % Metal | % Cl |
|---|---|---|---|---|---|---|
| 8 | C$_{14}$H$_{11}$N$_3$O$_2$ · ½Cu(NO$_3$)$_2$ | 48.50(48.61) | 3.26(3.20) | 16.45(16.19) | Cu 8.62(9.18) | |
| 9 | C$_{14}$H$_{11}$N$_3$O$_2$ · ½NiCl$_2$ · H$_2$O | 49.88(50.50) | 3.81(3.93) | 12.48(12.62) | Ni 8.64(7.91) | 10.46(10.46) |

*The number in parentheses represents the theoretical value as calculated from the Empirical Formula.

The 3-pyridylmethyl 4-substituted-phenylcarbamate metal salt complexes of the present invention can be formulated into rodenticidal compositions such as baits, tracking powders, and sprays. A bait comprises a semi-moist or dry edible carrier and the toxicant. A dry carrier is generally preferred. The carrier can be a combination of natural food products such as whole ground corn, corn meal, cornstarch, steel cut oats, sugar, milk powder, flour, molasses, rice, vegetable oil, salt, dehydrated fruit, fish meal, tankage, wheat or the like. When necessary to use in damp locations, a water repellent material, such as paraffin wax or an acrylic polymer, can be used as an additional carrier.

The metal salt complexes of the present invention may be incorporated as a toxicant in bait formulations, either alone or in combination with other toxicants. When used as the sole toxicant in baits, the compounds of the present invention may be used in any rodenticidally effective concentration. Depending on the susceptibility of the rodents to the toxicant and the amount of formulated bait generally consumed, concentrations as low as 0.1% by weight, and especially when intended for mice, even lower than 0.05%, and as high as 99% by weight, may be employed. A typical bait may contain between about 0.5% and 1.5% of the toxicant by weight.

Tracking powders, which are particularly effective against mice, may be either a metal salt complex of the present invention in finely powdered form or a mixture of the complex with powdered carrier, such as talc, sugar, milk powder, Indian corn meal, fish meal, cornstarch, flour, and bentonite, or the like, or any combination thereof which tends to induce the animals contaminated with the preparation to lick themselves more thoroughly. In tracking powders, a complex of the present invention may be incorporated in amounts from 100% down to 0.1% by weight with proper formulation. The following two examples describe the preparation of two typical rodenticidal formulations. However, wide variations in formulation for different conditions and locations of use are of course suitable.

EXAMPLE 10—BAIT FORMULATION

A 3-pyridylmethyl 4-substituted-phenylcarbamate metal salt complex is blended with a basal ration in a Waring laboratory blender to form 50 grams of a homogeneous premix. The amount of compound utilized is determined by the percentage of active material desired in the feed. The formula for a typical basal ration is shown below, all percentages being by weight:

| | |
|---|---|
| Crude gound corn | 65% |
| Steel cut oats | 25% |
| Powdered sugar | 5% |
| Corn oil | 5% |

The 50 grams of premix containing the toxicant are then mixed with an additional 450 grams of basal ration.

These components are mixed in a Little Ford Lodige mixer for three minutes, thus providing a suitable bait formulation.

EXAMPLE 11—TRACKING POWDER

A metal salt complex of the invention is finely pulverized by mortar and pestle to form a 100% active tracking powder. To form a 5% active material, the active complex is mixed with 10X confectioner's sugar in a 1 to 19 ratio. Other ratios can be used to give different concentrations of the active complex.

EXAMPLE 12—RODENTICIDAL ACTIVITY

The metal salt complexes of the invention are preliminarily evaluated for their ability to kill albino rats (*Rattus norvegicus*) by oral administration to two rats at a dosage of 50–200 mg/kg. In the standard test the effect on the rats is observed over a 14-day period. Table III gives the results of typical evaluations of metal salt complexes of this invention.

TABLE III

| | Rodenticidal Activity | |
|---|---|---|
| Example | Dosage (mg./kg.) | Mortalities No. Dead/Total No. |
| 1 | 50 | 2/2 |
| 2 | 50 | 1/2 |
| 3 | 50 | 2/2 |
| 3 | 200 | 1/2 |
| 4 | 50 | 2/2 |
| 5 | 50 | 2/2 |
| 6 | 50 | 2/2 |
| 7 | 50 | 2/2 |
| 8 | 50 | 2/2 |
| 9 | 50 | 2/2 |

It is to be understood that changes and variations may be made without departing from the spirit and scope of the invention as defined by the appended claims.

I claim:

1. A metal salt complex of the formula

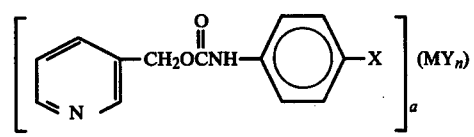

wherein
X is —NO$_2$, —CN, —CF$_3$, —SOR, —SO$_2$R, or —SO$_2$NH$_2$, wherein R is a (C$_1$–C$_4$)alkyl group;
M is an alkaline earth or transition metal cation;
Y is a bromide, chloride, iodide, perchlorate, carbonate, bicarbonate, nitrate, phosphate, sulfate, bisulfate, acetate, maleate, oxalate, or p-toluenesulfonate anion;
a is 1 or 2; and n is an integer which for the anion X satisfies the valence of the cation M.

2. The complex of claim 1 wherein X is —NO$_2$.

3. The complex of claim 2 wherein Y is chloride.

4. The complex of claim 3 wherein M is a zinc cation and a is 2.

5. The complex of claim 1 wherein X is —CN.

6. A metal salt complex which is the product formed by (a) contacting a salt of the formula MY$_n$, wherein M is an alkaline earth or transition metal cation;

Y is a bromide, chloride, iodide, perchlorate, carbonate, bicarbonate, nitrate, phosphate, sulfate, bisulfate, acetate, maleate, oxalate, or p-toluenesulfonate anion; and n is an integer which for the anion Y satisfies the valence of the cation M with a carbamate of the formula

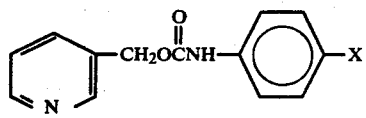

wherein X is —NO$_2$, —CN, —CF$_3$, —SOR, —SO$_2$R, or —SO$_2$NH$_2$, wherein R is a (C$_1$-C$_4$)alkyl group, in a solvent in which the salt and the carbamate have sufficient solubility to form a complex, and (b) partially or completely removing the solvent.

7. A rodenticidal composition which comprises a rodenticidally-effective amount of a complex according to claim 1 and an edible dry or semi-moist carrier.

8. The composition of claim 7 wherein the complex is present in an amount of at least about 0.05% by weight.

9. A method of exterminating pest rodents which comprises placing a rodenticidally effective amount of a complex according to claim 1 in the vicinity of a population of the pest rodents in a place where the complex may easily be reached and ingested by the pest rodents.

* * * * *